US006126669A

United States Patent [19]

Rijken et al.

[11] Patent Number: 6,126,669

[45] Date of Patent: Oct. 3, 2000

[54] DEPILATION SYSTEM

[75] Inventors: Martinus M. Rijken; Willem A. Westerhof; Matheus J. Van Der Meer, all of Drachten, Netherlands

[73] Assignee: U.S. Philips Corporation, New York, N.Y.

[21] Appl. No.: 09/024,634

[22] Filed: Feb. 17, 1998

[51] Int. Cl.[7] .......... A61B 17/32

[52] U.S. Cl. .......... 606/172

[58] Field of Search .......... 606/131, 36, 43, 606/133

[56] References Cited

U.S. PATENT DOCUMENTS

| | | | |
|---|---|---|---|
| 5,121,541 | 6/1992 | Patrakis | 30/41 |
| 5,133,130 | 7/1992 | Podolsky | 30/41 |
| 5,402,697 | 4/1995 | Brooks | 83/18 |

*Primary Examiner*—Michael Buiz
*Assistant Examiner*—Vy Q. Bui
*Attorney, Agent, or Firm*—Ernestine C. Bartlett

[57] ABSTRACT

The depilation system comprises an electric depilation apparatus and a cartridge (2). The depilation apparatus (1) comprises a depilation head (3), a drive unit (11), and a chamber (12) adapted to accommodate the cartridge (2). The cartridge (2comprises a reservoir (21) for holding a substance, a discharge channel (22), and a pump (23). The chamber extends between the depilation head and the drive unit. The depilation head is movable with respect to the depilation apparatus in such a manner that the chamber is accessible. In order to enable the pump to be actuated, the depilation apparatus comprises an actuator which extends into the chamber. A mechanism couples the actuator to a button at the exterior of the depilation apparatus (1) in such a manner that the actuator (13) can be driven by moving the button (15).

42 Claims, 5 Drawing Sheets

DEPILATION SYSTEM

BACKGROUND OF THE INVENTION

The invention relates to a depilation system comprising an electric depilation apparatus and a cartridge, which depilation apparatus comprises a depilation head having at least one drivable depilation element, a drive unit for driving the depilation element, and a chamber adapted to accommodate the cartridge, which cartridge comprises a reservoir for holding a substance, a discharge channel, and feeder means for conveying the substance from the reservoir to the discharge channel.

Such a depilation system is known from U.S. Pat. No. 5,402,697. The known depilation system comprises an electric shaving apparatus and a cartridge filled with a depilatory substance. The shaving apparatus comprises a shaving head, a driving unit and a deep chamber to accommodate the cartridge. Viewed from the shaving head, the chamber is disposed adjacent the drive unit and, at the side of the shaving apparatus which is remote from the shaving head, it has a cover to provide access to the chamber for mounting the cartridge. At the side of the shaving head the chamber communicates with a passage terminating at the exterior of the shaving head. The cartridge has an actuating button for dispensing the depilatory substance. The cover has an opening through which, in the closed condition of the cover, the button is accessible for a user when the cartridge has been mounted in the shaving apparatus. A drawback of the known system is that the chamber which accommodates the cartridge is difficult to clean. When the cartridge is inserted and removed said chamber may be soiled with residues of the substance. These residues readily give rise to the growth of bacteria, so that there is a risk of infection of the user of the shaving system. Another drawback of the known shaving system is that the cartridge is situated at a location which is best suited to mount a hair trimmer.

SUMMARY OF THE INVENTION

It is an object of the invention to provide a depilation system of the type defined in the opening paragraph, which is hygienic in use. To this end, the invention is characterized in that the chamber is disposed between the depilation head and the drive unit. This chamber is also referred to as a "hair chamber" because in this chamber the hairs are collected which are shaved off by the depilation head. For the users of a depilation apparatus having such a hair chamber the regular cleaning of the hair chamber is a familiar routine. Moreover, this chamber can be cleaned easily and effectively because it is a shallow chamber, so that the depilation system is hygienic in use. Besides, the chamber is readily accessible for mounting and removing the cartridge by removing the depilation head from the drive unit, as is customary with such a depilation apparatus, for the purpose of cleaning the hair chamber. The extension of an electric depilation apparatus to a depilation system by the addition of a cartridge containing a substance to be applied to the skin during depilation improves the depilation comfort. Owing to the measure in accordance with the invention this extension requires little additional attention from the user, as a result of which such a system is more likely to be successful.

An embodiment of the depilation system in accordance with the invention is characterized in that the depilation apparatus comprises an actuator for actuating the feeder means of the cartridge. By providing the depilation apparatus with an actuator the feeder means of the cartridge, for example a pump, can be driven without an actuating button being required on the cartridge. This actuator may comprise, for example, an element which can be given a reciprocating movement by a drive means and which transmits this movement to the pump. Alternatively, this actuator may comprise an element which is rotatable by a drive means and which transmits this rotation to the pump via a coupling.

An embodiment of the depilation system in accordance with the invention is characterized in that the depilation apparatus has a button at the exterior of the depilation apparatus, which button is coupled to the actuator via a mechanism for manually driving the actuator by moving the button. This measure enables the substance to be dispensed according to the user's need. Such an actuator drive can be manufactured at low cost. In addition, the transmission ratio of such a mechanism can be optimized in such a manner that only a small effort is needed to depress the button in order to apply the substance.

An embodiment of the depilation system in accordance with the invention is characterized in that the depilation apparatus comprises an electrical drive means for driving the actuator and control means for activating the drive means. These measures improve the user convenience. Thus, the control means can be coupled, for example, to the on/off switch of the depilation apparatus in such a manner that the substance is dispensed automatically when depilation begins. Moreover, the control means may include a timer for periodically activating the actuator during operation of the depilation apparatus. The actuator drive can be coupled, for example, to the drive unit for the depilation elements, so that only one motor is needed for the entire depilation apparatus.

An embodiment of the depilation system in accordance with the invention is characterized in that the depilation apparatus comprises a coupling element for coupling the depilation element to the drive unit, and the cartridge has a recess which corresponds to the position of the coupling element. In the case of a triple-head shaving apparatus, for example, the hair chamber is traversed by three coupling pins which couple the drive unit to cutters in the shaving head. As a result of this, there is not much space to accommodate a cartridge. By providing the cartridge with a recess the cartridge can extend between and partly around these pins, as a result of which the reservoir of the cartridge can have a reasonable volume which is adequate, for example, for one week of shaving.

BRIEF DESCRIPTION OF THE DRAWINGS

An embodiment of the depilation system in accordance with the invention is characterized in that the cartridge comprises a first part and a second part, which first part comprises locking means for locking the cartridge in the depilation apparatus and which second part comprises a flexible reservoir. By providing the cartridge with locking means, for example projections, the cartridge can be locked in the depilation apparatus by means of a snap connection. This locking assures an effective coupling between the actuator and the feeder means. By making the reservoir flexible it is achieved that a part of the substance can be pumped out of the reservoir without entry of air into the reservoir. Air in the reservoir is undesirable because it may give rise to degrading of the substance and because it may lead to air finding its way into the feeder means, so that the discharge of the substance becomes irregular or even stops completely. In addition, a flexible reservoir, for example in the form of a thin-walled plastic pouch, can be manufactured easily and cheaply and its shape readily adapts to the shape of the chamber.

An embodiment of the depilation system in accordance with the invention is characterized in that the depilation head has a discharge opening and coupling means for coupling the discharge opening to the discharge channel. By providing the depilation head with a discharge opening for applying the substance to the skin of the user the substance can be applied during depilation without having to interrupt the depilation process. In comparison with a system in which the discharge channel of the cartridge extends up to the exterior of the depilation head this embodiment has the advantage that a smooth surface of the depilation head is guaranteed independently of tolerances in the dimensioning of the depilation apparatus and the cartridge. Besides, the depilation head may be provided with channels near the discharge opening in order to assure better spreading of the substance.

An embodiment of the depilation system in accordance with the invention is characterized in that the feeder means include a diaphragm pump. A diaphragm pump can be made of a small number of simple parts. Preferably, all the parts are made of a plastic. This enables the whole cartridge to be replaced at moderate cost when the reservoir is empty. This promotes the hygiene.

An embodiment of the depilation system in accordance with the invention is characterized in that the chamber is accessible by moving the depilation head with respect to the drive unit. As a result of this, the chamber becomes even better accessible, which facilitates cleaning of the chamber and further reduces the risk of growth of bacteria.

The invention also relates to a depilation apparatus and to the cartridge of the depilation system in accordance with the invention.

DESCRIPTION OF THE PREFERRED EMBODIMENTS

Figure 1:
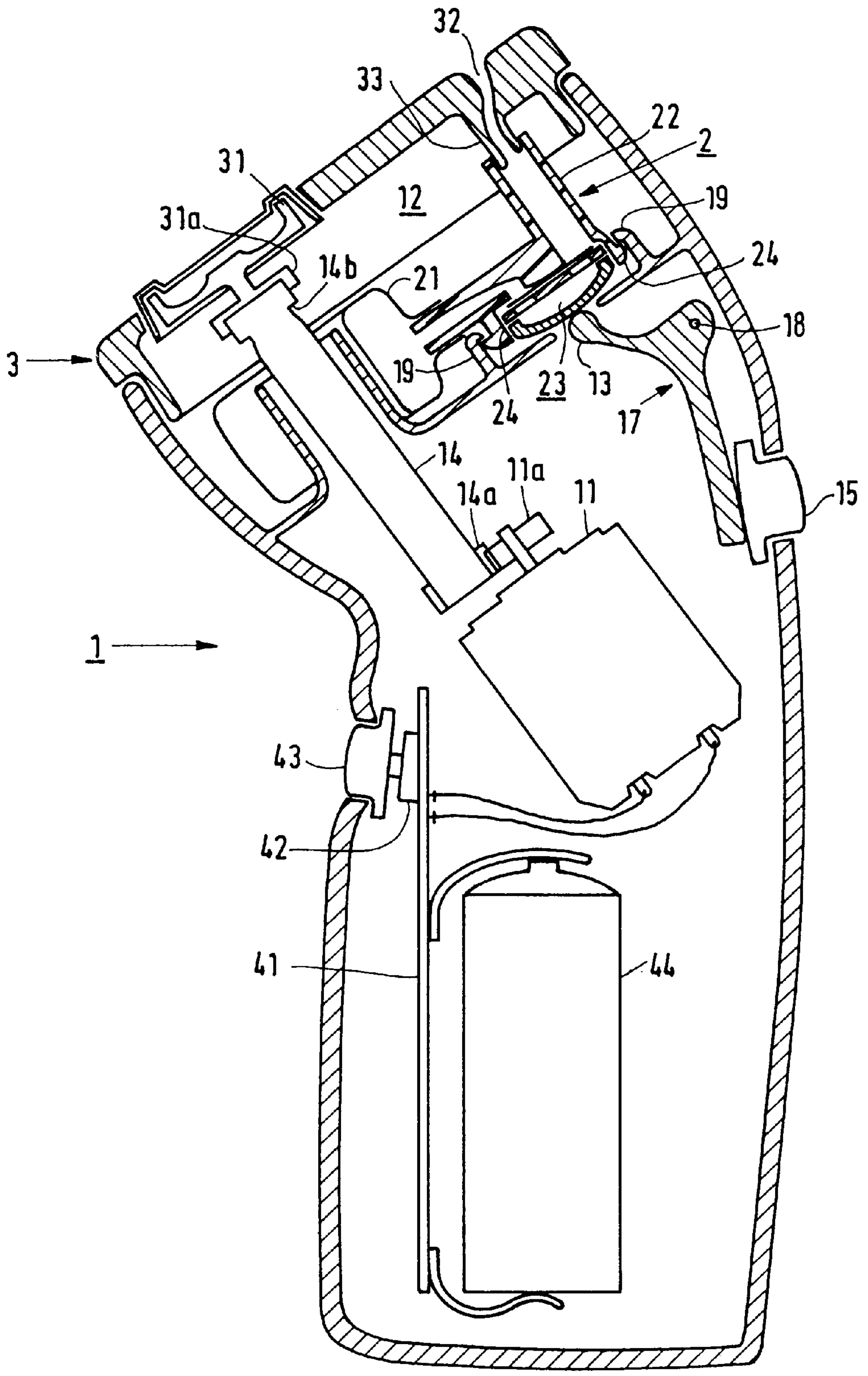
Figure 2:
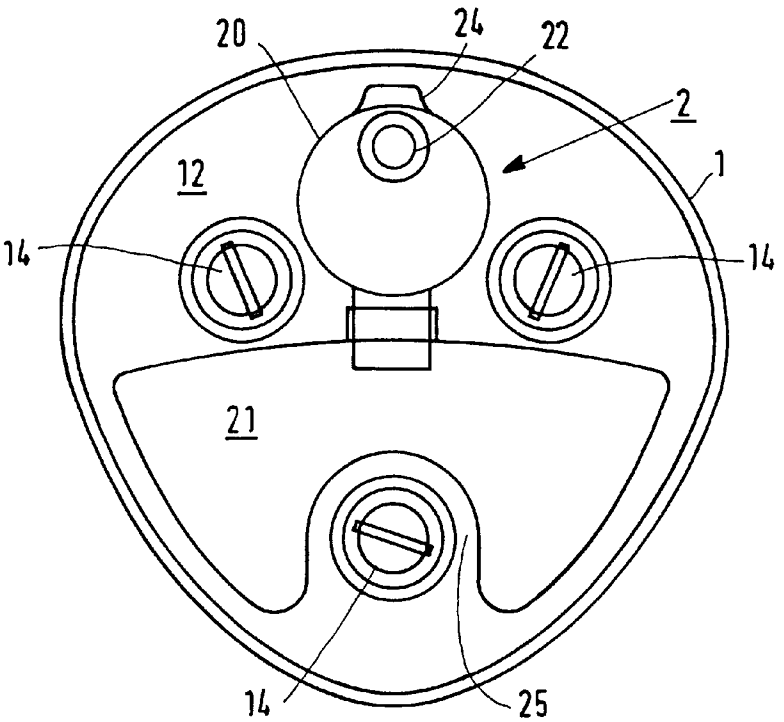
Figure 3:
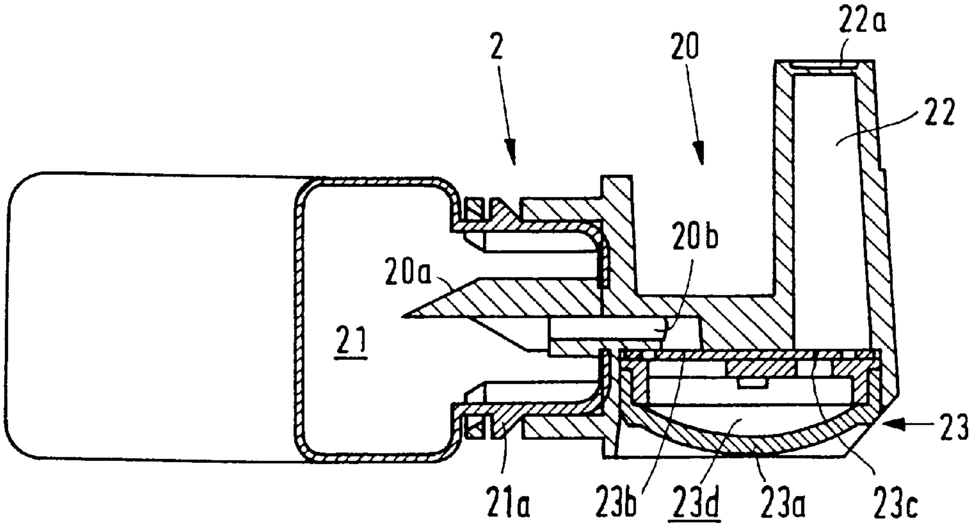
Figure 4:
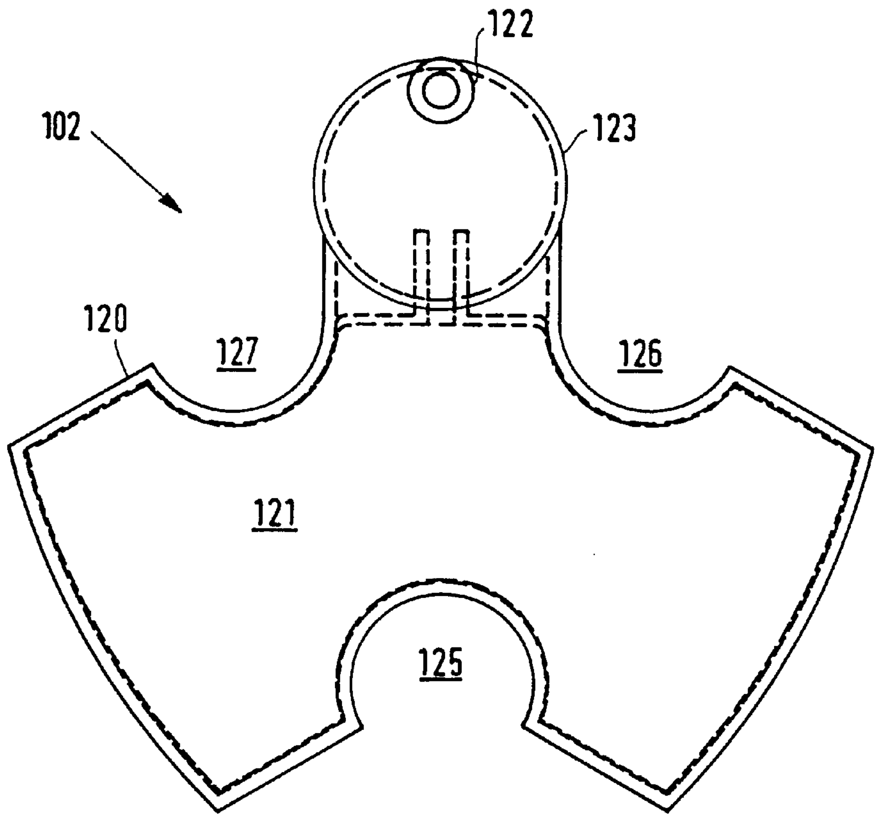
Figure 5:
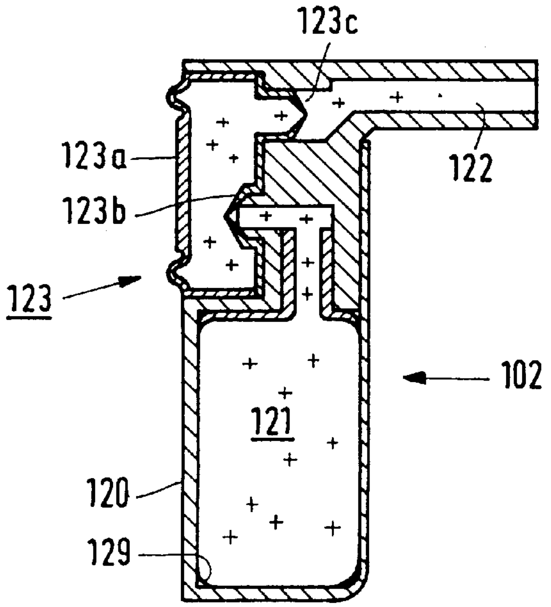
Figure 6:
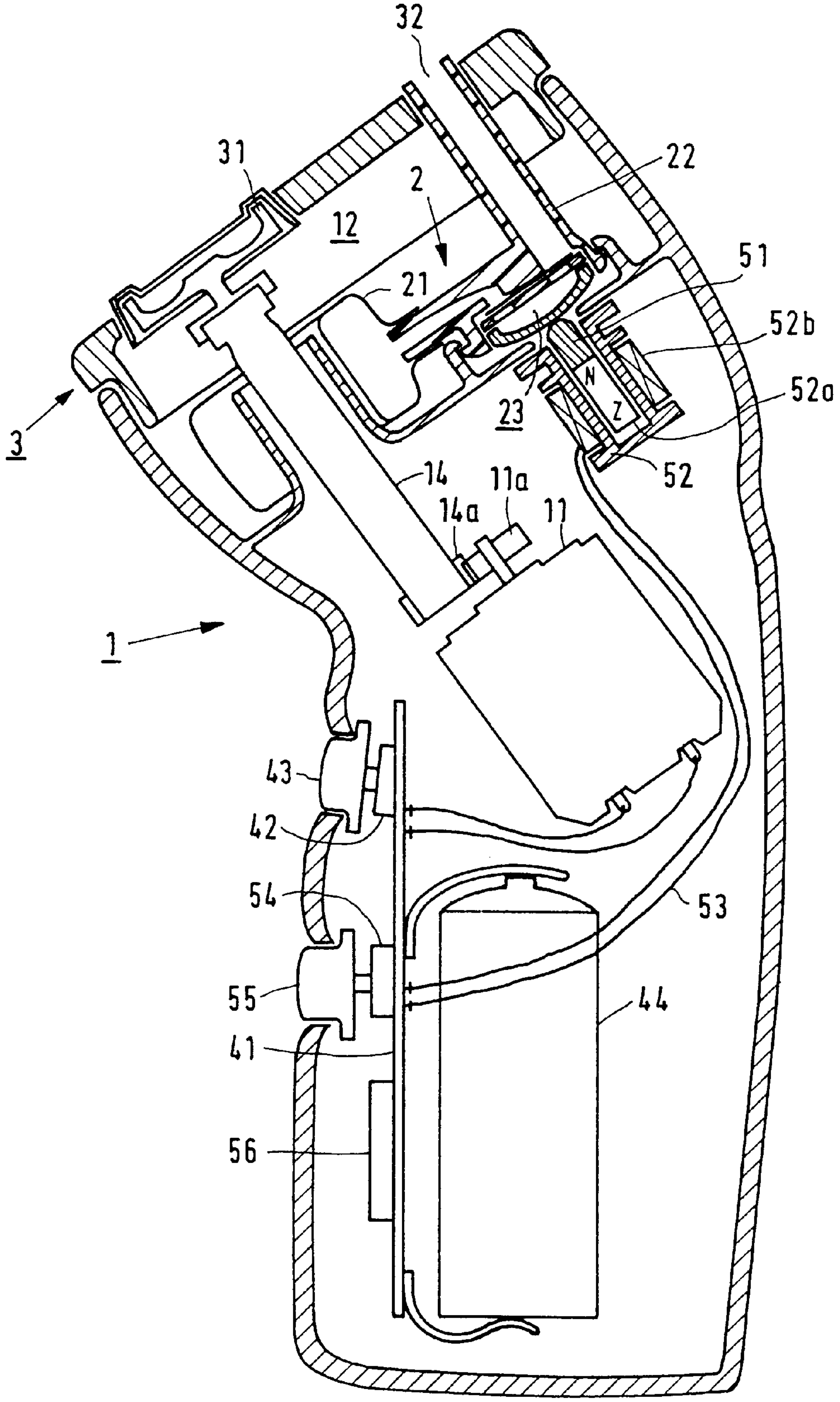
Figure 7:
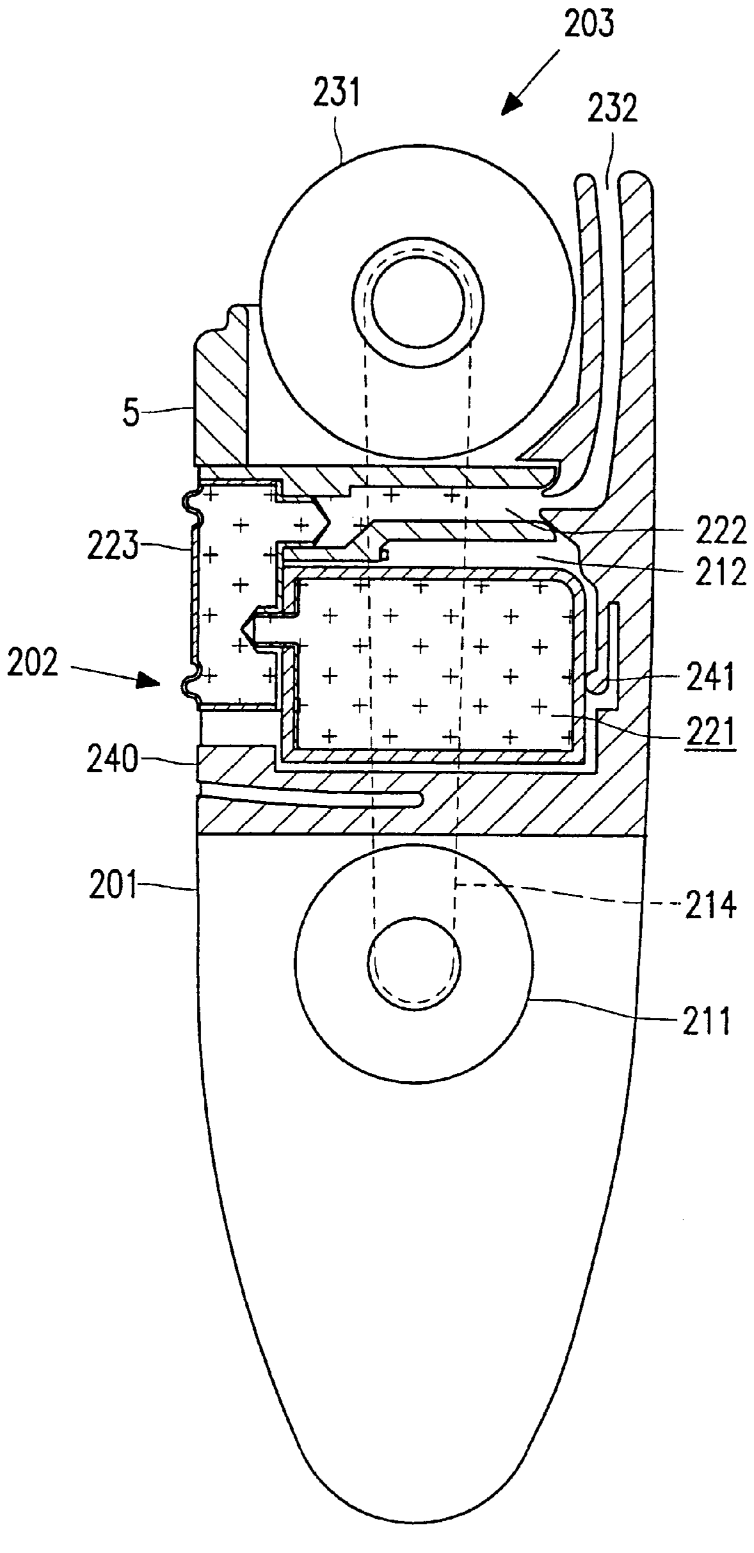

The invention will now be described in more detail, by way of example, with reference to the drawings, in which FIG. 1 is a sectional view of a first embodiment of the depilation system in accordance with the invention, FIG. 2 is a plan view showing the first embodiment of the invention with the depilation head removed, FIG. 3 is a sectional view showing a cartridge for the depilation system in accordance with the invention, FIG. 4 is a plan view showing an alternative cartridge for the depilation system in accordance with the invention, FIG. 5 is a sectional view showing this alternative cartridge, FIG. 6 shows a second embodiment of the depilation system in accordance with the invention, and FIG. 7 shows a third embodiment of the depilation system in accordance with the invention.

DETAILED DESCRIPTION OF THE PREFERRED EMBODIMENTS

FIG. 1 shows a first embodiment of the depilation system in accordance with the invention. The depilation system comprises an electric shaving apparatus 1 and a cartridge 2. The shaving apparatus 1 comprises a shaving head 3 with drivable cutters 31, of which one cutter is shown. The shaving apparatus 1 further has a drive unit, comprising an electric motor 11 for driving the cutters 31 and further having a chamber 12 adapted to accommodate the cartridge 2. The cartridge 2 has a reservoir 21 for holding a substance. This substance may serve, for example, to reduce the friction between the shaving head 3 and the skin of a user. The cartridge 2 has a discharge channel 22 and feeder means for conveying the substance from the reservoir 21 to the discharge channel 22. The chamber 12 extends between the shaving head 3 and the drive unit 11. The shaving head 3 is movable with respect to the shaving apparatus 1 in such a manner that the chamber 12 is accessible. The shaving head 3 can be attached to the shaving apparatus 1, for example, via a snap connection. Alternatively, the shaving head 3 can be attached to the shaving apparatus 1 via a hinge, not shown. The chamber 12 is readily accessible by removing the shaving head 3 or hinging it open. As a result of this, the chamber 12 can be cleaned properly and the cartridge 2 can readily be fitted and removed. In order to keep the cartridge 2 in position the shaving apparatus 1 comprises hooks 19 which engage with locking means, in the present case hooks 24, of the cartridge 2. The hooks 19 and 24 are shaped in such a manner that the cartridge 2 can be fitted and removed by exerting some force.

In the present case the feeder means 23 comprise a diaphragm pump (see FIG. 3) for feeding the substance from the reservoir 21 to the discharge channel 22. The shaving head 3 has a discharge opening 32 and coupling means, in the present case a tubular portion 33, for coupling the discharge opening 32 to the discharge channel 22. To enable the diaphragm pump 23 to be actuated, the shaving apparatus 1 comprises an actuator 13 which extends into the chamber 12. A mechanism, in the present case a lever 17 which is pivotable about a pivot 18, couples the actuator 13 to a button 15 at the exterior of the shaving apparatus 1, in such a manner that the actuator 13 can be driven by moving the button 15. When the button 15 is pressed the diaphragm 23*a* (see FIG. 3) is depressed and a small amount of the substance can be applied to the skin of a user via the discharge opening 32.

The chamber 12 is traversed by a coupling element 14 which serves for coupling the drive mechanism 11 to the cutter 31. The coupling element 14 carries a toothed ring 14*a* which is in mesh with a pinion 11*a* mounted on the shaft of the motor 11. Near the shaving head 3 the coupling element 14 comprises a coupling portion 14*b* which engages with a coupling portion 31*a* connected to the cutter 31. The coupling portions 14*b* and 31*a* are locked in rotation when the shaving head 3 is mounted on the shaving apparatus 1. When the shaving head 3 is removed or hinged open the coupling portions 31*a* and 14*b* are disengaged from each other. The tubular portion 33 and the discharge channel 22 are also disengaged from one another during this removal or hinging open.

The shaving apparatus 1 further comprises a battery 44, which can be coupled to the motor 11 via a switch 42 mounted on a printed circuit board 41. The switch 42 can be actuated by means of a button 43 at the exterior of the shaving apparatus 1.

FIG. 2 is a plan view of the first embodiment of the shaving system in accordance with the invention shown in FIG. 1 with the shaving head 3 removed. The Figure clearly shows that the chamber 12 is readily accessible when the shaving head 3 has been removed from the shaving apparatus 1. In this embodiment the shaving apparatus 1 comprises three coupling elements 14 which traverse the chamber 12. The cartridge 2 is disposed between the coupling elements 14. The cartridge 2 comprises a first part 20 and a second part 21. The first part 20 comprises the discharge channel 22, locking means 24, and the diaphragm pump (not shown). The second part is formed by a flexible reservoir 21. The reservoir 21 has a centrally disposed recess 25 which corresponds to the position of one of the coupling elements 14. As a result of this measure, a substantial part of the volume of the chamber 12 can be utilized despite the presence of the coupling elements 14.

FIG. 3 is a sectional view of the cartridge 2 for the depilation system in accordance with the invention. The first part 20 is essentially formed by a hard plastic injection-molded product. The reservoir 21 has a collar 21*a* comprising elements for coupling the reservoir 21 to the first part 20. The first part 20 comprises a hollow needle 20*a* by means of which an opening is made in the reservoir 21 when the reservoir 21 is coupled to the first part 20. The reservoir 21 is coupled to the diaphragm pump 23 via the channel 20*b* in the needle 20*a*. The diaphragm pump 23 comprises a chamber 23*d* bounded by a diaphragm 23*a*. The volume of the chamber 23*d* can be varied by depressing the diaphragm 23*a*. To obtain a pumping action the diaphragm pump 23 comprises two valves 23*b* and 23*c* made of a flexible material, for example rubber. When the diaphragm 23*a* is depressed the volume of the chamber 23*d* is reduced, the valve 23*c* opens and a part of the contents of the chamber 23*d* is pumped to the discharge channel 22. When the diaphragm 23*a* is released it will resume its initial position owing to its elasticity and the volume of the chamber 23*d* will increase. As a result of this, the valve 23*b* will open and a part of the contents of the reservoir 21 will be drawn to the chamber 23*d* via the channel 20*b*. By repeatedly depressing and releasing the diaphragm 23*a* the contents of the reservoir 21 can be pumped to the discharge channel 22. The wall of the reservoir 21 consists of a thin plastic film. As a result, the volume of the reservoir 21 will decrease when a part of the contents of the reservoir 21 is pumped out of the reservoir. This prevents the entry of air into the reservoir 21.

The discharge channel 22 of the cartridge 2 is sealed by means of a membrane 22*a* before the cartridge is used. As a result of this, the entire discharge channel 22 and the pump chamber 23*d* can be filled with the substance during manufacture of the cartridge without this substance being directly exposed to the environment. When the cartridge 2 is placed into a shaving apparatus 1 (see FIG. 1) and the shaving head 3 is replaced on the shaving apparatus the tubular portion 33 of the shaving head 3 perforates the membrane 22*a* of the cartridge 2. As a result, the discharge opening 32 and the discharge channel 22 are coupled. Filling the chamber 23*d* and the discharge channel 22 with the substance has the advantage that the cartridge 2 can contain a larger amount of the substance. In addition, this has the advantage that after the cartridge 2 has been placed into the shaving apparatus 1 substance will be discharged from the discharge opening 32 almost immediately upon actuation of the diaphragm pump 23.

FIG. 4 is a plan view showing an alternative cartridge for the shaving system in accordance with the invention. The cartridge 102 has a hard plastic housing 120 in which a reservoir 121, a diaphragm pump 123 and a discharge channel 122 are situated. The housing 120 has three recesses 125, 126 and 127 corresponding to the positions of the coupling elements 14 shown in FIG. 2.

FIG. 5 is a sectional view of the alternative cartridge shown in FIG. 4. In order to preclude contact between the substance and the atmosphere the reservoir 121 is surrounded by a thin and flexible inner wall 129. The hard plastic housing 120 protects the thin-walled reservoir, which results in a more robust cartridge 102. Similarly to the manner described with reference to FIG. 3, the diaphragm pump 123 pumps the substance to the discharge channel 122 via the valves 123*b* and 123*c* by repeatedly depressing and releasing the diaphragm 123*a*.

FIG. 6 is a sectional view of a second embodiment of the shaving system in accordance with the invention. The difference with the first embodiment of the shaving system in accordance with the invention is that the shaving apparatus 1 comprises an electrical drive means 52 for driving the actuator and that the discharge channel 22 of the cartridge 2 projects from the shaving head 3. In the present example, the electrical drive means 52 comprises a magnet 52*a* connected to an actuator 51. The magnet 52*a* is drivable by feeding a current through the coil 52*b*. With the aid of control means, in the present case a button 55 at the exterior of the shaving apparatus and a switch 54, the coil 52*a* is coupled to a battery 44 via a wiring 53. The actuator 51 is activated by pressing the button 55. The control means may include a control circuit 56 which feeds a current pulse through the coil 52*b* at regular intervals in dependence upon the positions of the switches 54 and/or 42. In this way a regular supply of substance can be obtained during shaving. By having the discharge channel 22 of the cartridge 2 project from the shaving head 3 a coupling between the discharge channel opening and the discharge channel as shown in FIG. 2 can be dispensed with.

FIG. 7 shows a third embodiment of the depilation system in accordance with the invention. The depilation system comprises an electrical depilation apparatus 201 and a cartridge 202. The depilation apparatus 201 has a depilation head 203 comprising drivable depilation discs 231, of which one disc is shown. The depilation apparatus 201 further has a drive unit comprising an electric motor 211 for driving the depilation discs 231 and also has a chamber 212 adapted to accommodate the cartridge 202. The cartridge 202 has a reservoir 221 for holding a substance. This substance may be, for example, a skin-care product for the skin of a user. The cartridge 202 has a discharge channel 222 and a diaphragm pump 223 for conveying the substance from the reservoir 221 to the discharge channel 222. The chamber 212 extends between the depilation head 203 and the drive unit 211. The cartridge 202 can be removed by depressing the resilient latch 240, after which the cartridge 202 is urged slightly outward by the resilient element 241 and can be removed. Thus, the chamber 212 is readily accessible and can be cleaned properly. A toothed belt 214 adjacent the chamber 212 serves for coupling the drive mechanism 211 to the depilation discs 231.

It is to be noted that the invention is not limited to the embodiments shown herein by way of examples. Various other embodiments are possible within the scope of the invention. For example, the feeder means for conveying the substance from the reservoir to the discharge channel can be formed by an open channel, the volume of the reservoir being reduced step by step by means of an actuator in the form of a flat plate. It is also possible to use another type of pump, for example a reciprocating pump. In addition, it is possible to arrange the pump in a central position relative to the reservoir or to accommodate a plurality of reservoirs in the cartridge. Instead of the electromagnetic drive means of the actuator shown herein it is also possible to use a piezoelectric drive. The invention can be used with similar advantages in a shaving apparatus with a vibratory cutter.

What is claimed is:

1. A depilation system comprising an electric depilation apparatus and a cartridge, which depilation apparatus comprises a depilation head having at least one drivable depilation element, a drive unit for driving the depilation element, and a chamber adapted to accommodate the cartridge, which cartridge comprises a reservoir for holding a substance, a discharge channel, and feeder means for conveying the substance from the reservoir to the discharge channel, wherein the chamber is disposed between the depilation head and the drive unit.

2. A depilation system as claimed in claim 1, wherein the depilation apparatus comprises an actuator for actuating the feeder means of the cartridge.

3. A depilation system as claimed in claim 2, wherein the depilation apparatus has a button at the exterior of the depilation apparatus, which button is coupled to the actuator via a mechanism for manually driving the actuator by moving the button.

4. A depilation system as claimed in claim 3, wherein the depilation apparatus comprises a coupling element for coupling the depilation element to the drive unit, and the cartridge has a recess which corresponds to the position of the coupling element.

5. A depilation system as claimed in claim 3, wherein the cartridge comprises a first part and a second part, which first part comprises locking means for locking the cartridge in the depilation apparatus and which second part comprises a flexible reservoir.

6. A depilation system as claimed in claim 3, wherein the depilation head has a discharge opening and coupling means for coupling the discharge opening to the discharge channel.

7. A depilation system as claimed claim 3, wherein the feeder means comprise a diaphragm pump.

8. A depilation system as claimed in claim 3, wherein the chamber is accessible by moving the depilation head with respect to the drive unit.

9. A depilation system as claimed in claim 2, wherein the depilation apparatus comprises an electrical drive means for driving the actuator and control means for activating the drive means.

10. A depilation system as claimed in claim 9 wherein the depilation apparatus comprises a coupling element for coupling the depilation element to the drive unit, and the cartridge has a recess which corresponds to the position of the coupling element.

11. A depilation system as claimed in claim 9, wherein the cartridge comprises a first part and a second part, which first part comprises locking means for locking the cartridge in the depilation apparatus and which second part comprises a flexible reservoir.

12. A depilation system as claimed in claim 9, wherein the depilation head has a discharge opening and coupling means for coupling the discharge opening to the discharge channel.

13. A depilation system as claimed claim 9, wherein the feeder means comprise a diaphragm pump.

14. A depilation system as claimed in claim 9, wherein the chamber is accessible by moving the depilation head with respect to the drive unit.

15. A depilation system as claimed in claim 2 wherein the depilation apparatus comprises a coupling element for coupling the depilation element to the drive unit, and the cartridge has a recess which corresponds to the position of the coupling element.

16. A depilation system as claimed in claim 2, wherein the cartridge comprises a first part and a second part, which first part comprises locking means for locking the cartridge in the depilation apparatus and which second part comprises a flexible reservoir.

17. A depilation system as claimed in claim 2, wherein the depilation head has a discharge opening and coupling means for coupling the discharge opening to the discharge channel.

18. A depilation system as claimed claim 2, wherein the feeder means comprise a diaphragm pump.

19. A depilation system as claimed in claim 2, wherein the chamber is accessible by moving the depilation head with respect to the drive unit.

20. A depilation system as claimed in claim 1, wherein the depilation apparatus comprises a coupling element for coupling the depilation element to the drive unit, and the cartridge has a recess which corresponds to the position of the coupling element.

21. A depilation system as claimed in claim 20, the cartridge comprises a first part and a second part, which first part comprises locking means for locking the cartridge in the depilation apparatus and which second part comprises a flexible reservoir.

22. A depilation system as claimed in claim 20, wherein the depilation head has a discharge opening and coupling means for coupling the discharge opening to the discharge channel.

23. A depilation system as claimed claim 20, wherein the feeder means comprise a diaphragm pump.

24. A depilation system as claimed in claim 20, wherein the chamber is accessible by moving the depilation head with respect to the drive unit.

25. A depilation system as claimed in claim 1, wherein the cartridge comprises a first part and a second part, which first part comprises locking means for locking the cartridge in the depilation apparatus and which second part comprises a flexible reservoir.

26. A depilation system as claimed in claim 25, wherein the depilation head has a discharge opening and coupling means for coupling the discharge opening to the discharge channel.

27. A depilation system as claimed claim 25, wherein the feeder means comprise a diaphragm pump.

28. A depilation system as claimed in claim 25, wherein the chamber is accessible by moving the depilation head with respect to the drive unit.

29. A depilation system as claimed in claim 1, wherein the depilation head has a discharge opening and coupling means for coupling the discharge opening to the discharge channel.

30. A depilation system as claimed claim 29, wherein the feeder means comprise a diaphragm pump.

31. A depilation system as claimed in claim 29, wherein the chamber is accessible by moving the depilation head with respect to the drive unit.

32. A depilation system as claimed in claim 1, wherein the feeder means comprise a diaphragm pump.

33. A depilation system as claimed in claim 32, wherein the chamber is accessible by moving the depilation head with respect to the drive unit.

34. A depilation system as claimed in claim 1, wherein the chamber is accessible by moving the depilation head with respect to the drive unit.

35. A depilation apparatus comprising a depilation head having at least one drivable depilation element, a drive unit for driving the depilation element, and a chamber adapted to accommodate a cartridge, in which the chamber is disposed between the depilation head and the drive unit.

36. A depilation apparatus as claimed in claim 35, wherein the depilation apparatus comprises an actuator for actuating the feeder means of the cartridge.

37. A depilation apparatus as claimed in claim 36, wherein the depilation apparatus has a button at the exterior of the depilation apparatus, which button is coupled to the actuator via a mechanism for manually driving the actuator by moving the button.

38. A depilation apparatus as claimed in claim 37, wherein the chamber is accessible by moving the depilation head with respect to the drive unit.

39. A depilation apparatus as claimed in claim 36, wherein the depilation apparatus comprises an electrical drive means for driving the actuator and control means for activating the drive means.

40. A depilation apparatus as claimed in claim 39, wherein the chamber is accessible by moving the depilation head with respect to the drive unit.

41. A depilation apparatus as claimed in claim 36, wherein the chamber is accessible by moving the depilation head with respect to the drive unit.

42. A depilation apparatus as claimed in claim 35, wherein the chamber is accessible by moving the depilation head with respect to the drive unit.

* * * * *